United States Patent [19]

Johnston

[11] Patent Number: 4,954,488
[45] Date of Patent: Sep. 4, 1990

[54] METHOD OF TREATING HYPERALDOSTERONISM USING 17β-CYCLOPROPYLAMINOANDROSTENE DERIVATIVES

[75] Inventor: J. O'Neal Johnston, Milford, Ohio

[73] Assignee: Merrell Dow Pharmaceuticals Inc., Cincinnati, Ohio

[21] Appl. No.: 366,551

[22] Filed: Jun. 14, 1989

[51] Int. Cl.$^5$ .............................................. A61K 31/56
[52] U.S. Cl. ...................................... 514/177; 514/182
[58] Field of Search .................................. 514/177, 182

[56] References Cited

U.S. PATENT DOCUMENTS 3,639,598  2/1972  Klimstra ............................... 514/182
4,891,367  1/1990  Angelastro et al. ................. 514/177

FOREIGN PATENT DOCUMENTS 0288053  10/1988  European Pat. Off. .
1027746  4/1966  United Kingdom .

OTHER PUBLICATIONS

Davis, et al., *J. Chem. Soc., C, Org.*, 19, 1688 (1966).
B. J. Taylor, M. S. Thesis, Massachusetts Institute of Technology, 1985, pp. 2, 24–26 (*Incomplete*), Abstract and Figures.

*Primary Examiner*—Joseph A. Lipovsky
*Attorney, Agent, or Firm*—John J. Kolando

[57] ABSTRACT

The present invention is directed to a method for the treatment of hyperaldosteronism and related disorders which comprises administering to an appropriate patient an appropriate 17β-cyclopropylaminoandrostene.

6 Claims, No Drawings

METHOD OF TREATING HYPERALDOSTERONISM USING 17β-CYCLOPROPYLAMINOANDROSTENE DERIVATIVES

BACKGROUND OF THE INVENTION

A. Chemistry

European Patent Application No. 0 288 053, published Oct. 26, 1988, describes the preparation of 17β-(cyclopropylamino)androst-5-en-3β-ol and related compounds and indicates that those compounds are useful in the treatment of androgen-dependent disorders. British patent No. 1,027,746 describes a variety of steroids having a variety of 17-amine substituents. The most relevant substituent of this type would appear to be (mononuclear cycloalkyl)amine wherein the cycloalkyl group is defined as containing 3 to 8 carbon atoms. However, the only compounds of this type specifically described in the patent contain a cyclohexyl group. No other cycloalkyl group is even named in the patent. In addition, the compounds in the patent are described as possessing central stimulant activity but there is no elaboration on that activity and there is no suggestion of the inhibition of aldosterone biosynthesis.

B. Utility

Aldosterone is a steroidal hormone which is synthesized in the zona glomerulosa cells of the adrenal glands. The primary biological function of this compound is the regulation of salt retention and, in particular, aldosterone plays a major role in controlling the reabsorption of sodium ions from the urine by the kidney. Thus, a deficiency of the enzyme responsible for the synthesis of aldosterone is a characteristic of patients with a salt-losing syndrome, while primary hyperaldosteronism can result from hyperbiosynthesis of aldosterone as caused by an adrenocortical tumor or the administration of certain drugs. The hyperaldosteronism may involve hypertension, hypokalemia, alkalosis, muscular weakness, polyuria and polydipsia. Thus, treatment of hyperaldosteronism and the conditions associated with it would be possible by blockage of the enzymatic synthesis of aldosterone.

SUMMARY OF THE INVENTION

The present invention relates to the use of certain 17-cyclopropylamino derivatives of androstene as aldosterone inhibitors.

DETAILED DESCRIPTION OF THE INVENTION

The present invention relates to a method for treating hyperaldosteronism which comprises administering to a patient having said condition a therapeutically effective amount of a 17-cyclopropylaminoandrostene of the formula

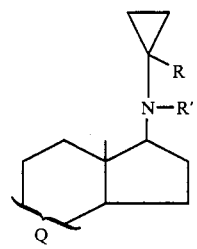

wherein R is hydrogen or methyl; R' is hydrogen, $C_1$–$C_4$ alkyl or cyclopropyl; and Q is

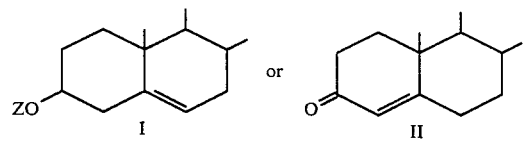

wherein Z is hydrogen, alkanoyl of 1–10 carbon atoms, cyclopentane-alkanoyl or benzene-alkanoyl wherein the alkanoyl portion of the cyclopentane-alkanoyl or benzene-alkanoyl contains up to 4 carbon atoms. Examples of alkanoyl groups are acetyl, propionyl, butanoyl, and decanoyl; examples of the cyclopentane- and benzene-alkanoyl groups are cyclopentanepropionyl and benzenepropionyl. Preferred compounds are those in which Q is structure II.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for examples, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acids.

A preferred embodiment of the present invention relates to a method for treating hyperaldosteronism which comprises administering to a patient having said condition 17β-(cyclopropylamino)androst-4-en-3-one or 17β-[N-methyl(cyclopropylamino)]androst-4-en-3-one.

More specifically, the present invention relates to the use of the indicated compounds to inhibit the synthesis of aldosterone and thus for use in a method for the treatment of conditions in which such inhibition would be desired. Thus, the indicated compounds are useful in a method for the treatment of hyperaldosteronism and various conditions wherein a reduction of the excessive amount of aldosterone responsible for the condition would be beneficial. That is, they are useful in a method for the general treatment of hyperaldosteronism and any associated hypertension, edema and/or sodium retention whether this is the result of some bodily disorder or whether it results from the administration of some agent. As a result of their effect on the factors responsible for edema and/or sodium retention, the indicated compounds would be useful in a method for treatment as diuretic agents.

The activity of the indicated compounds as aldosterone inhibitors and, thus, their utility in a method for treating hyperaldosteronism can be demonstrated by the following procedure which measures the inhibition of enzymes in the synthesis of aldosterone.

Young male Sprague-Dawley rats were maintained on a sodium-deficient diet for about two weeks prior to use. From these animals, adrenal capsule/glomerulosa homogenates were prepared (6 mg/ml) in pH 7.4 assay buffer [$MgCl_2$ 8.5 mM, $CaCl_2$ 2.7 mM, KCl 3.13 mM, NaCl 7.591 mM, TRIS 50 mM and 0.1% triethylamine] and centrifuged 500xg for 10 minutes.

Assays were conducted in 35 ml glass tubes maintained at 25° C. in a Dubnoff shaker with 95% $O_2$/5% $CO_2$. The tubes contained the following material: 100 μl of an NADPH+ generating system, 300 μl of adrenal capsular/glomerulosa cytosol, and 50 μl of test compound or buffer (control). After initial preincubation intervals of 20 minutes, the 10-minute assay was started by the addition of 50 μl of tritium-labelled substrate, i.e., 1 μM [$^3$H]-DOC. Reactions were quenched by the addition of 5 ml of ethyl acetate and non-radiolabelled steroids were also added. The samples were extracted twice with 5 ml of ethyl acetate and the solvent evaporated under nitrogen at 30°–40° C.

Residues were redissolved in methanol:water (40:60) with 0.1% triethylamine and high performance liquid chromatography was used to separate products on a C18 reverse phase (5μ ODS-Hypersil) column (4.6×250 mm, Shannon) with a 1 ml/min flow rate using an MeOH:$H_2O$ gradient (solvent A 10/90:solvent B 90/10).

Substrate remaining and products formed were monitored by UV absorbance at 246 nM and the amount of steroid compound present was quantified by [$^3$H] radioactivity. The concentration of compound to produce half-maximal inhibition ($IC_{50}$) of aldosterone formation from the 40 minute preincubation data was graphically estimated from a linear-log plot of percent inhibition vs. log of the compound concentration. The $K_i$ for time-dependent inhibition and the $t_{\frac{1}{2}}$ for enzyme inactivation at infinite inhibitor concentration ($t_{50}$) was determined by the linear regression analyses of $t_{\frac{1}{2}}$ vs. 1/[I] data of Kitz-Wilson plots. Using this procedure, the following results were observed:

| Test Compound | $IC_{50}$ (μM) | $K_i$ (μM) | $t_{50}$ (min) |
|---|---|---|---|
| 17β-(Cyclopropyl-amino)androst-4-en-3-one | 0.18 | — | — |
| 17β-(Cyclopropyl-amino)androst-5-en-3β-ol | 1.10 | 4.85 | 9.7 |
| 17β-[N-Methyl(cyclopropylamino)]androst-4-en-3-one | 0.13 | 0.14 | 15.4 |
| 17β-[N-Methyl(cyclopropylamino)]-androst-5-en-3β-ol | 0.35 | 0.35 | 9.0 |

The above results demonstrate the effectiveness of 17β-cyclopropylaminoandrostenes as inhibitors of aldosterone biosynthesis according to the method of the present invention. The 17β-[N-methyl(cyclopropylamino)]androst-4-en-3-one was obtained from the corresponding 5-en-3β-ol by the same procedure described in EP No. 0 288 053 for the preparation of 17β-(cyclopropylamino)androst-4-en-3-one.

To achieve a particular desired effect, such as a diuretic effect, in the method of the present invention, the compounds as described above can be administered orally or parenterally, for example, intramuscularly and subcutaneously, to a patient in need of treatment. The term patient is taken to mean a warm-blooded mammal such as rats, mice, dogs, cats, horses, pigs, cows, sheep and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration, the amount of compound administered, that is, the diuretic effective amount, is from 0.1 to 150 mg/kg of body weight per day and preferably from 1 to 50 mg/kg of body weight per day. Unit dosages for oral or parenteral administration may contain, for example, from 5 to 200 mg of the active ingredient. The compounds can be administered alone or in combination with one another, or in combination with other diuretics.

For oral administration, the compounds can be formulated into solid or liquid preparations, such as capsules, pills, tablets, troches, powders, solutions, suspensions or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation. Sustained release can also be achieved by use of an appropriately formulated transdermal patch.

The following are illustrative pharmaceutical formulations suitable for oral or parenteral administration which may be employed in practicing the present invention:

TABLET

| | | |
|---|---|---|
| (a) 17β-[N-Methyl(cyclopropylamino)]-androst-4-en-3-one | 75.0 g | |
| (b) Lactose | 1.216 kg | |
| (c) Corn starch | 0.3 kg | |

Mix the active ingredient, the lactose, and the corn starch uniformly. Granulate with 10% starch paste. Dry to a moisture content of about 2.5%. Screen through a No. 12 mesh screen. Add and mix the following:

| | |
|---|---|
| (a) Magnesium stearate | 0.015 kg |
| (b) Corn starch qs ad | 1.725 kg |

Compress on a suitable tablet machine to a weight of 0.115 g/tablet.

| IM INJECTIONS (Oil Type) | |
|---|---|
| (a) 17β-[N-Methyl(cyclopropylamino)]-androst-4-en-3-one | 25.0 mg |
| (b) BHA, BHT aa | 0.01 % w/v |
| (c) Peanut oil or sesame oil qs | 1.0 ml |

What is claimed is:

1. A method for treating hyperaldosteronism which comprises administering to a patient having said condition a therapeutically effective amount of a compound of the

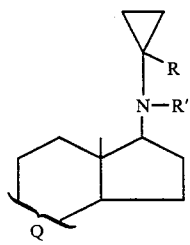

wherein R is hydrogen or methyl; R' is hydrogen, $C_1$-$C_4$ alkyl or cyclopropyl; and Q is

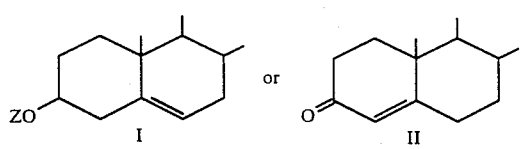

wherein Z is hydrogen, alkanoyl of 1–10 carbon atoms, cyclopentane-alkanoyl or benzene-alkanoyl wherein the alkanoyl portion of the cyclopentane-alkanoyl or benzene-alkanoyl contains up to 4 carbon atoms.

2. A method according to claim 1 for treating hyperaldosteronism which comprises administering to a patient having said condition a therapeutically effective amount of a compound of the formula

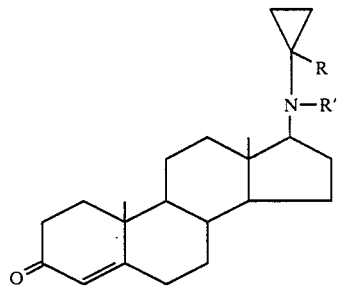

wherein R is hydrogen or methyl; and R' is hydrogen or $C_{1-4}$ alkyl.

3. A method according to claim 1 for treating hyperaldosteronism which comprises administering to a patient having said condition a therapeutically effective amount of 17β-[N-methyl(cyclopropylamino)]androst-4-en-3-one.

4. A method for producing a diuretic effect which comprises administering to a patient in need of such treatment an effective amount of a compound of the formula

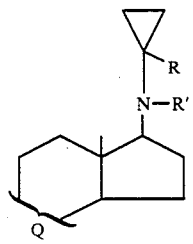

wherein R is hydrogen Or methyl; R' is hydrogen, $C_1$-$C_4$ alkyl or cyclopropyl; and Q is

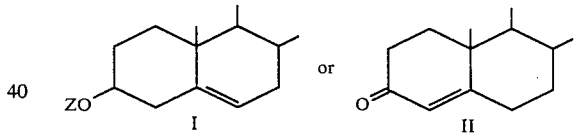

wherein Z is hydrogen, alkanoyl of 1–10 carbon atoms, cyclopentane-alkanoyl or benzene-alkanoyl wherein the alkanoyl portion of the cyclopentane-alkanoyl or benzene-alkanoyl contains up to 4 carbon atoms.

5. A method according to claim 4 for producing a diuretic effect which comprises administering to a patient in need of such treatment a therapeutically effective amount of a compound of the formula

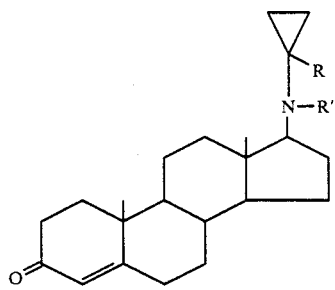

wherein R is hydrogen or methyl; and R' is hydrogen or $C_{1-4}$ alkyl.

6. A method according to claim 4 for producing a diuretic effect which comprises administering to a patient in need of such treatment a therapeutically effective amount of 17β-[N-methyl(cyclopropylamino)]androst-4-en-3-one.

* * * * *

UNITED STATES PATENT AND TRADEMARK OFFICE
CERTIFICATE OF

PATENT NO. : 4,954,488
DATED : September 4, 1990
INVENTOR(S) : J. O'Neal Johnston It is certified that error appears in the above-identified patent and that said Letters Patent is hereby corrected as shown below:

Column 3, Line 34 reads: "$H_2o$" and should read -- $H_2O$ --.

Column 5, Line 35 reads: "of the" and should read -- of the formula --.

Signed and Sealed this

Third Day of December, 1991

Attest:

HARRY F. MANBECK, JR.

*Attesting Officer*    *Commissioner of Patents and Trademarks*